United States Patent [19]

Haugwitz et al.

[11] 4,093,732
[45] June 6, 1978

[54] SULFOXIDE DERIVATIVES OF BENZIMIDAZOLES

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 769,634

[22] Filed: Feb. 17, 1977

[51] Int. Cl.$^2$ .................. C07D 235/32; A61K 31/415
[52] U.S. Cl. .................................. 424/273 R; 548/306
[58] Field of Search ...................... 260/309.2; 424/273; 548/306

[56] References Cited

U.S. PATENT DOCUMENTS 3,929,821  12/1975  Beard et al. .......................... 424/273
4,002,640  1/1977  Beard et al. ......................... 260/309.2

FOREIGN PATENT DOCUMENTS 809,234  6/1974  Belgium ............................ 260/309.2

*Primary Examiner*—Natalie Trousof
*Attorney, Agent, or Firm*—Lawrence S. Levinson; Merle J. Smith; Burton Rodney

[57] ABSTRACT

Sulfoxide derivatives of benzimidazoles are provided having the structure

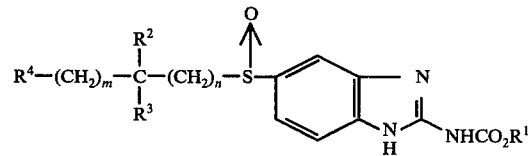

wherein $R^1$ is lower alkyl or phenyl-lower alkyl, $R^2$ and $R^3$ may be the same or different and are hydrogen or lower alkyl, $R^4$ is alkylcycloalkyl, halocycloalkyl or cycloalkenyl, and $m$ is 0 to 3, $n$ is 0 to 3, $m + n$ being < 5. These compounds are useful as anthelmintic agents.

13 Claims, No Drawings

SULFOXIDE DERIVATIVES OF BENZIMIDAZOLES

BACKGROUND OF THE INVENTION

Various benzimidazole compounds are known for their use as anthelmentic agents, such as disclosed in U.S. Pat. Nos. 3,928,821, 3,929,822, 3,929,823, 3,929,824, 3,935,209, 3,965,113, 4,002,640 and 4,005,202 all to Beard et al and assigned to Syntex; 3,574,845 and 3,682,952 to Actor, 3,578,676 and 3,694,455 to Dunn, 3,915,986 and 3,969,526 to Gyurik, all assigned to Smith Kline; 3,738,993 to Haugwitz et al.

U.S. Pat. No. 4,002,640 discloses benzimidazole compounds which have the structure

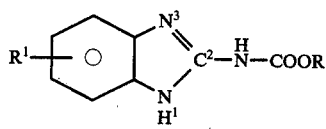

wherein R is lower alkyl having 1 to 4 carbon atoms, $R^1$ may be $-SOR^2$, and $R^2$ may be lower alkyl having from 1 to 6 carbons, cycloalkyl having 3 to 7 carbons, lower alkenyl or lower alkynyl having 3 to 6 carbons, or aralkyl or aryl. The $R^1$ alkyl group may be optionally substituted with one or more radicals such as thiocyanato, alkoxy, aryl, aroyl, hydroxy, cycloalkyl, halo, cyano or nitro radicals. Specific compounds disclosed include 5(6)-cyclopropylmethylsulfinyl-2-carbomethoxyaminobenzimidazole, 5(6)-cyclopentylsulfinyl-2-carbomethoxyaminobenzimidazole, 5(6)-cyclohexylsulfinyl-2-carbomethoxyaminobenzimidazole, 5(6)-ethylsulfinyl-2-carbomethoxyaminobenzimidazole, 5(6)-n-butylsulfinyl-2-carbomethoxyaminobenzimidazole, 5(6)-n-propylsulfinyl-2-carbomethoxyaminobenzimidazole, 5(6)-phenylsulfinyl-2-carbomethoxyaminobenzimidazole, and 5(6)-benzylsulfinyl-2-carbomethoxyaminobenzimidazole. These compounds as well as the benzimidazoles disclosed in all of the aforementioned patents are said to be active perorally in the treatment of helminthiasis.

U.S. Pat. Nos. 3,954,791 to Loewe et al and 3,928,375 to Düwel et al, both assigned to Hoechst disclose 2-carbalkoxy-amino-benzimidazole-5(6)-phenyl ethers (and thioethers) which are said to be active perorally as well as subcutaneously.

DESCRIPTION OF THE INVENTION

The present invention relates to sulfoxide derivatives of benzimidazoles having the structure

I $R^4-(CH_2)_m-\underset{\underset{R^3}{|}}{\overset{\overset{R^2}{|}}{C}}-(CH_2)_n-S$—[benzimidazole with NHCO$_2$R$^1$]

wherein $R^1$ is lower alkyl or phenyl-lower alkyl, $R^2$ and $R^3$ may be the same or different and are hydrogen or lower alkyl, and $R^4$ is alkylcycloalkyl, halocycloalkyl, or cycloalkenyl, $m$ is 0 to 3, $n$ is 0 to 3 and $m + n$ is $\leq$ 5.

The term "halogen" or "halo" as used throughout the specification refers to fluorine, chlorine, bromine, and iodine; chlorine is preferred.

The term "lower alkyl" as used herein includes straight or branched chain aliphatic hydrocarbon radicals having up to and including seven carbon atoms, such as methyl, ethyl, propyl, isopropyl, butyl, isobutyl, t-butyl, amyl, hexyl, heptyl and the like.

$(CH_2)_m$ and $(CH_2)_n$ represent a single bond or straight or branched chain alkylene radicals containing 3 or less carbons in the longest normal chain.

The term "phenyl lower alkyl" as used herein refers to lower alkyl groups as discussed above having a phenyl substituent, such as benzyl.

The terms "alkylcycloalkyl" and "halocycloalkyl" include cyclic hydrocarbon groups containing 3 to 12 carbons substituted with 1, 2 or 3 halogen groups or 1, 2 or 3 alkyl groups. The term "cycloalkenyl" includes cyclic hydrocarbon groups containing 3 to 10 carbons which may optionally be substituted with 1, 2 or 3 halogen groups or 1, 2, 3 alkyl groups. Examples of suitable cycloalkyl and cycloalkenyl groups include 2,2-dichloro-cyclopropyl, 2-methyl-cyclobutyl, 3-methyl-cyclopentyl, 2,4-dimethyl-cyclohexyl, 2-bromo-cycloheptyl, 3,4-dichloro-cyclooctyl, 2,4,6-triethyl-cyclodecyl and 3-chloro-cyclododecyl, cyclopropenyl, cyclobutenyl, cyclohexenyl, cycloheptenyl, cyclononenyl and cyclodecenyl, any of which cycloalkenyl groups may be substituted with 1, 2 or 3 halogen or lower alkyl groups. In the above cycloalkenyl rings, the double bond may be at any position in the ring.

Preferred are those compounds wherein $R^1$ is methyl, ethyl, propyl or benzyl, $m$ is 0, $n$ is 0 or 1, $R^2$ is hydrogen or methyl, $R^3$ is hydrogen, $R^4$ is 2,2-dichloro-cyclopropyl or cyclohexen-3-yl.

Examples of preferred compounds falling within the present invention include the following.

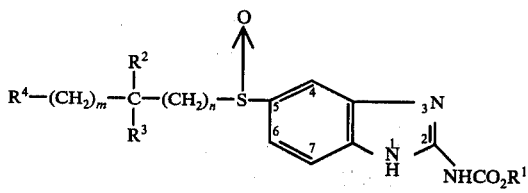

| | $R^1$ | $R^2$ | $R^3$ | $R^4$ | $(CH_2)_m$ | $(CH_2)_n$ |
|---|---|---|---|---|---|---|
| 1. | CH$_3$ | H | H | △ | — | — |
| 2. | CH$_3$ | H | H | CH$_3$-cyclohexyl-CH$_3$ | — | — |
| 3. | CH$_3$ | H | H | Cl,Cl-cyclopropyl | — | — |
| 4. | C$_2$H$_5$ | CH$_3$ | H | C$_2$H$_5$-cyclopropyl | — | — |
| 5. | CH$_3$ | H | H | cyclohexyl | — | — |
| 6. | C$_6$H$_5$CH$_2$ | H | H | Cl,Cl-cyclopropyl | — | — |
| 7. | C$_3$H$_7$ | H | H | cyclopentyl | — | — |
| 8. | CH$_3$ | H | H | cycloheptenyl | — | — |

-continued

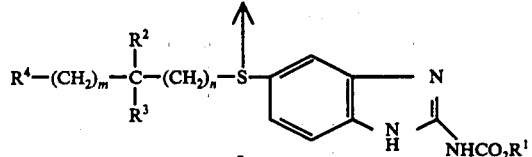

| | R¹ | R² | R³ | R⁴ | (CH₂)ₘ | (CH₂)ₙ |
|---|---|---|---|---|---|---|
| 9. | C₆H₅CH₂ | H | H | CH₃ (tetramethylcyclohexyl) | — | — |
| 10. | C₃H₇ | H | H | (methylcyclohexyl) | — | — |
| 11. | C₆H₅CH₂ | H | H | (methylcyclohexyl) | — | — |
| 12. | CH₃ | H | H | (dichlorocycloheptyl with CH₃) | — | — |
| 13. | CH₃ | H | H | (bromo, methylcyclopropyl) | — | — |
| 14. | CH₃ | H | C₂H₅ | (cyclohexyl) | CH₂ | — |
| 15. | C₂H₅ | H | H | (cyclopropyl) | — | CH₂ |
| 16. | C₃H₇ | CH₃ | CH₃ | (cyclopentenyl) | CH₂ | CH₂ |

The benzimidazole derivatives of structure I may be prepared by thiocyanation of o-nitroaniline to yield 4-thiocyano-2-nitroaniline (II). This product is then subjected to a sodium borohydride reduction to yield the corresponding 4-mercapto-2-nitroaniline (III). The mercapto derivative may be isolated or used directly for the next step. Thus, to the reaction mixture there is added the haloalkyl cycloalkane or haloalkyl cycloalkene IV to furnish the sulfide V which preferably is converted to its acetyl derivative.

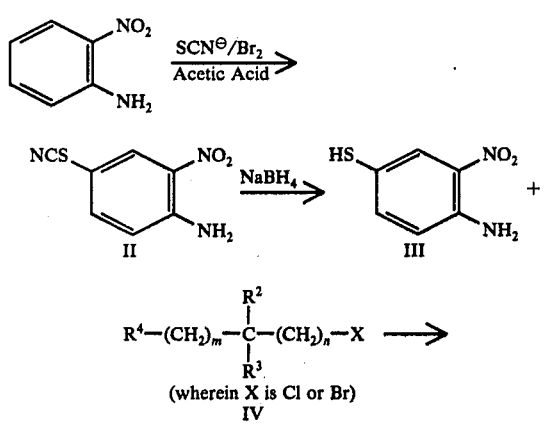

(wherein X is Cl or Br)
IV

-continued

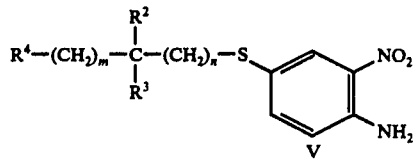

The sulfides of structure V (preferably their acetyl derivatives) are converted to the corresponding sulfoxides by oxidizing agents such as hydrogen peroxide, peracids (e.g., peracetic acid, m-chloroperbenzoic acid), manganese dioxide, sodium metaperiodate as outlined by Sandler and Caro (Organic Functional Group Preparations, 1968, p. 493).

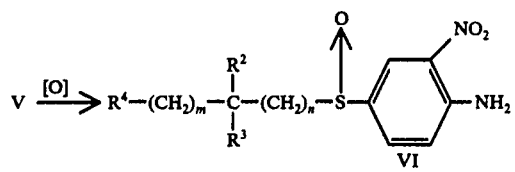

The resulting sulfoxides VI may be purified by crystallization and then reduced to the corresponding o-phenylene diamine VII. Either chemical or catalytic reduction may be used. For the chemical reduction the procedure outlined by Sandler and Caro (Organic Functional Group Preparations, 1968, pp. 339–340) is preferred. The final step in the synthesis of I, namely ring closure of VII to furnish I, can be achieved in various ways. Whereas refluxing of VII with the isolated thiourea derivative VIII in alcohols such as methanol or ethanol will furnish I, the preferred method of preparing I is by forming VIII in situ and then without isolating it adding VII and refluxing it for 30 minutes to 5 hours to yield the desired product.

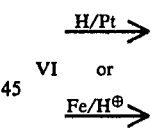

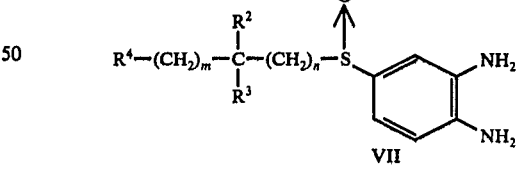

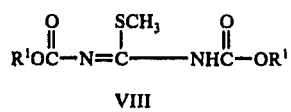

An alternative route toward the intermediate VII offers the reaction of IX with the requisite mercaptoalkyl cycloalkane or cycloalkene X, to yield XI. Here, in contrast to the alkylation step described above, (i.e., III → V) the reaction temperature has to be higher and the reaction periods have to be longer. Oxidation of XI yields the sulfoxide XII which on reduction furnishes the diamine VII.

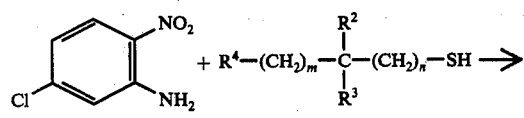
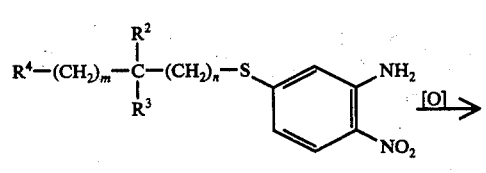
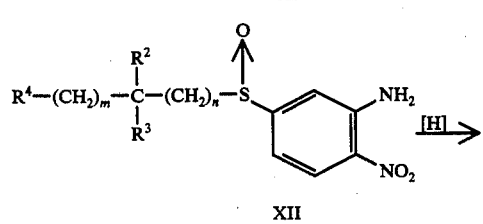
Compounds of structure I may also be synthesized by converting intermediate V into the o-phenylenediamine XIII as outlined above which is then cyclized to the benzimidazole XIV. The final step, i.e., oxidation of XIV, yields I.
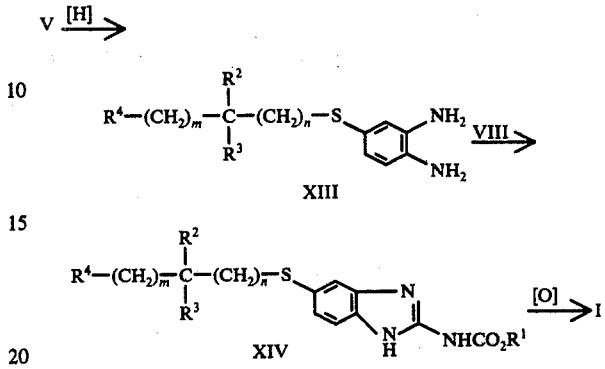
Examples of suitable haloalkyl cycloalkanes and haloalkyl cycloalkenes of formula IV suitable for use herein include the following.
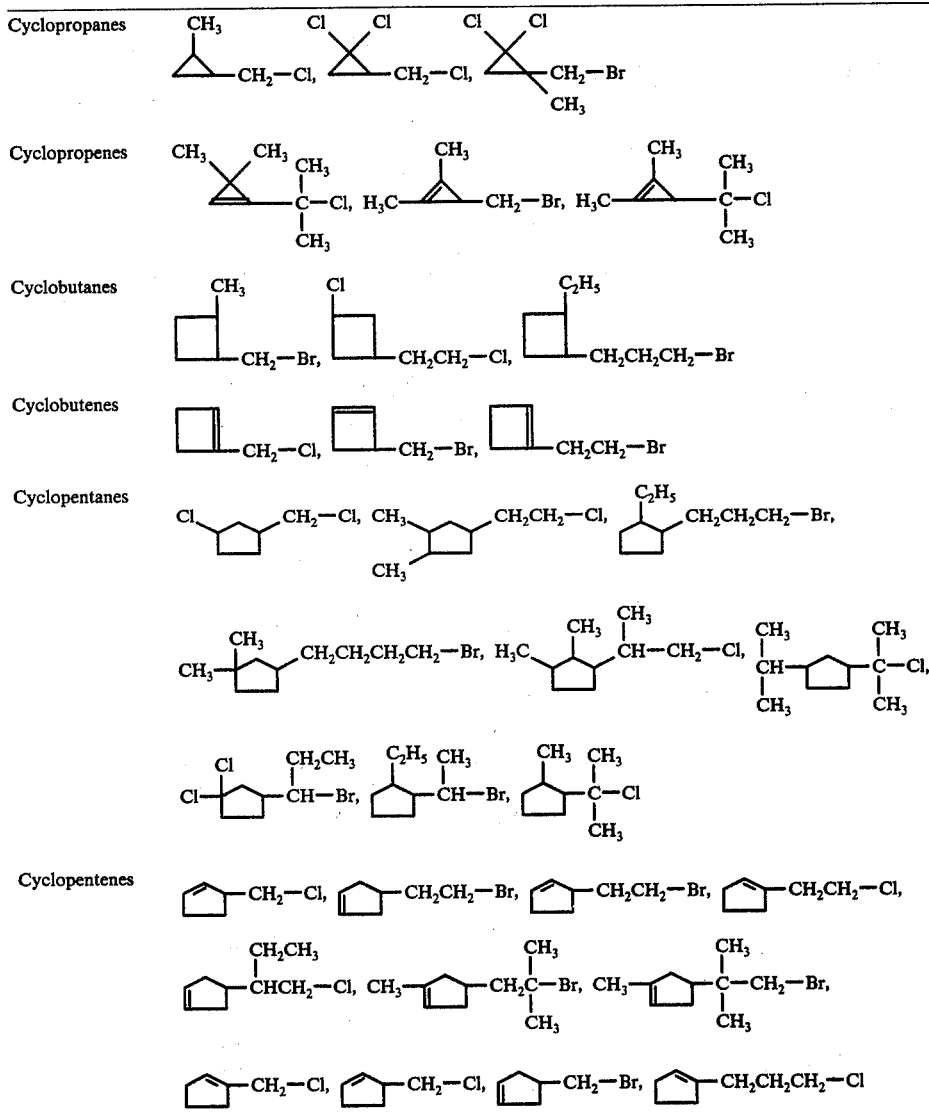

-continued
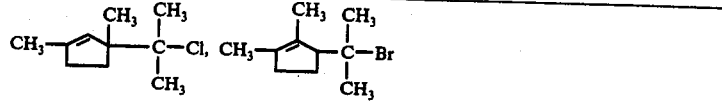
Cyclohexanes 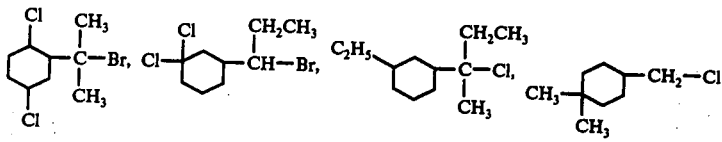
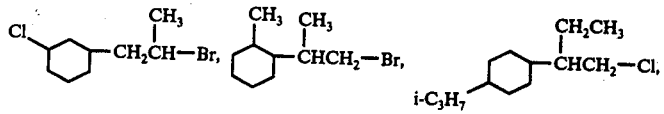
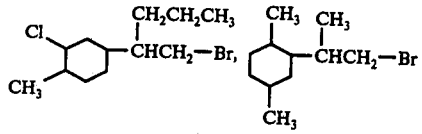
Cyclohexenes 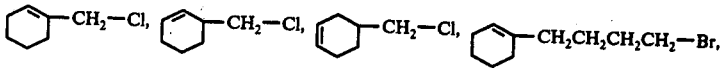
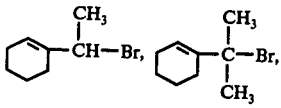
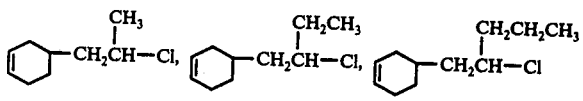
Cycloheptanes 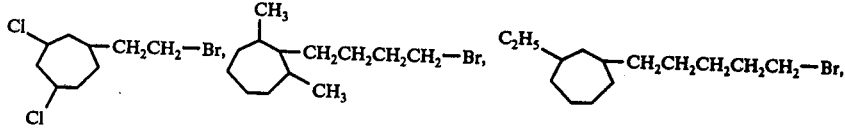
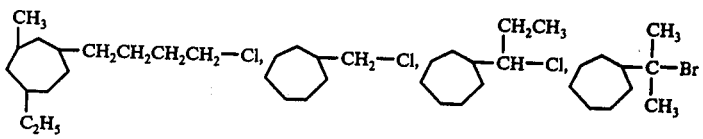
Cycloheptenes 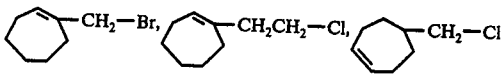
Cyclooctanes 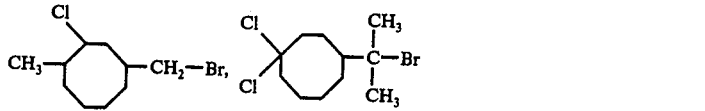
Cyclooctenes 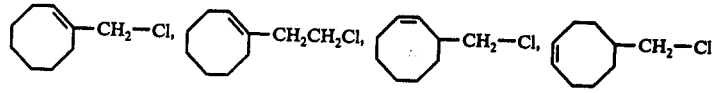
Cyclononanes 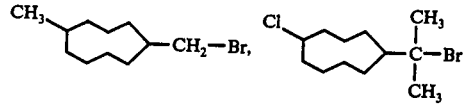
Cyclononenes 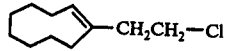
Cyclodecanes 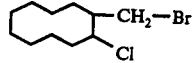

| | |
|---|---|
| Cyclodecenes | 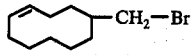 |
| Cycloundecanes | 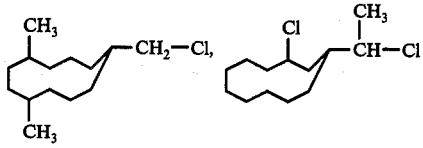 |
| Cyclododecenes |  |

A great variety of haloalkyl cycloalkanes IV are commercially available. In some cases the requisite haloalkyl cycloalkane has to be synthesized. For example, the addition of dichlorocarbene to allyl bromide furnishes the cyclopropyl derivative IV

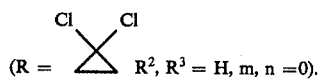

Additions of other than dichlorocarbene are possible, such as, monochlorocarbene, dibromocarbene, and the like.

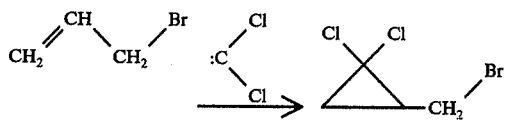

The requisite haloalkyl cycloalkanes or cycloalkenes may also be prepared from the corresponding alcohols by standard reactions.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomun, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5-25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1-2%. Lastly, feeds containing the active ingredient may be made directly by mixing said active ingredient in a feed which is inert to said anthelmintic compounds so as to give feeds having concentrations of anthelmintic agent of from 0.1-2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

[5-[(2,2-Dichlorocyclopropylmethyl)sulfinyl]-1H-benzimidazol-2-yl]carbamic acid, methyl ester

A.

4-[(2,2-dichlorocyclopropyl)methyl]thio-2-nitroaniline

To a stirred mixture of 11.75 g (0.06 mole) of 2-nitro-4-thiocyanoaniline in 500 ml of absolute ethanol under $N_2$ there is added 2.5 g (0.06 mole) of sodium borohydride in portions. The mixture is stirred at room temperature for 15 minutes and then refluxed for 15 minutes. The heating mantle is removed and 3.9 g (0.06 mole) of KOH in 30 ml of absolute ethanol is added. The mixture is stirred for 1 minute. A solution of 12.25 g (0.06 mole) of 1-bromomethyl-2,2-dichlorocyclopropane in 30 ml of absolute ethanol is added and the mixture is stirred at room temperature for 15 minutes and then refluxed for 2 hours. Equal amounts of $H_2O$ and $CHCl_3$ are added until 2 layers are formed. The organic layer is separated, dried ($MgSO_4$), and the solvent removed in vacuo to give a red oil which is chromatographed on silica gel. Elution with ethyl ether gives 9.6 g of red oil.

B.

4-[(2,2-Dichlorocyclopropyl)methyl]thio-o-phenylenediamine

A mixture of 8.8 g (0.03 mole) of 4-[(2,2-dichlorocyclopropyl)methyl]thio-2-nitroaniline and 0.6 g of $PtO_2$ in 200 ml of absolute ethanol is reduced on the Parr hydrogenator at 50 psi until the theoretical amount of $H_2$ is absorbed. The mixture is filtered and the solvent is removed in vacuo to yield a dark oil.

C.

[5-[(2,2-Dichlorocyclopropylmethyl)thio]-1H-benzimidazol-2-yl]carbamic acid, methyl ester To a mixture of 9 g of 2-methyl-2-thiopseudourea sulfate in 6 ml of $H_2O$ there is added 5.7 ml of methyl chloroformate at 0° C and the mixture is stirred for 15 minutes. Then there is added 12 ml of 25% NaOH dropwise and the mixture is stirred for 15 minutes. Then there is added 6 ml of acetic acid dropwise and the mixture is stirred for 15 minutes. Then the total amount of 4-[(2,2-dichlorocyclopropyl)methyl]thio-o-phenylenediamine from above in 50 ml of methanol is added and the mixture is refluxed for 2 hours. The alcohol is removed in vacuo and $H_2O$ is added. The resulting solid is filtered off and crystallized from glyme to yield 5.4 g, m.p. 211–213°.

D.

[5-[(2,2-Dichlorocyclopropylmethyl)sulfinyl]-1H-benzimidazol-2-yl]carbamic acid, methyl ester To a solution of 3.4 g of [5-[(2,2-dichlorocyclopropylmethyl)thio]-1H-benzimidazol-2-yl]carbamic acid, methyl ester in 50 ml of $CHCl_3$ and 50 ml of HOAc at −20° C there is added 2.1 g m-chloroperbenzoic acid in 20 ml of $CHCl_3$. The mixture is allowed to reach room temperature and then is stirred for 4 hours. $CHCl_3$ is removed in vacuo and the solution is neutralized with NaOH. The resulting oil solid is filtered and crystallized from glyme-ethyl ether to give the title compound.

EXAMPLE 2

[5-[[(2,2-Dichloro-1-methylcyclopropyl)methyl]sulfinyl]-1H-benzimidazol-2-yl]carbamic acid, methyl ester

A.

[5-[[(2,2-Dichloro-1-methylcyclopropyl)methyl]-thio]-1H-benzimidazol-2-yl]carbamic acid, methyl ester To a vigorously stirred mixture of 45.3 g (0.5 mole) of 3-chloro-2-methylpropene, 120 g of chloroform and 1.5 g of benzyltriethylammonium chloride (TEBA) there is added dropwise 120 ml of 50% NaOH not allowing the temperature to rise above 40° C. The mixture is kept at 35–40° C for 3 hours then diluted with 250 ml of $H_2O$ and extracted with chloroform. The organic layer is dried ($MgSO_4$) and the $CHCl_3$ removed in vacuo. Distillation of the residue under house vacuum yields 1,1-dichloro-2-chloromethyl-2-methylcyclopropane, b.p. 89–90° C, 45.7 g yield.

To a stirred mixture 9.75 g (0.05 mole) of 2-nitro-4-thiocyanoaniline in 500 ml of absolute ethanol under $N_2$, there is added 2.1 g of sodium borohydride in portions. The mixture is stirred at room temperature for 3 hours. 3.25 g (0.05 mole) of KOH in 30 ml of absolute ethanol is added. The mixture is stirred for 1 minute. A solution of 8.7 g (0.05 mole) of 1,1-dichloro-2-chloromethyl-2-methylcyclopropane in 15 ml of absolute ethanol is added and the mixture is refluxed for 3 hours. Equal amounts of $H_2O$ and $CHCl_3$ are added until two layers are formed. The organic layer is separated, dried ($MgSO_4$), and the solvent removed in vacuo to give a red oil which is triturated with 10 ml of absolute ethanol to yield 9.6 g of 2-nitro-4-[(2,2-dichloro-1-methylcyclopropyl)methyl]thioaniline as a solid, m.p. 76–78° C.

A mixture of 9.0 g (0.03 mole) of 2-nitro-4-[(2,2-dichloro-1-methylcyclopropyl)methyl]thioaniline and 0.9 g of $PtO_2$ in 200 ml of absolute ethanol is reduced on the Parr hydrogenator at 50 psi until the theoretical amount of $H_2$ is absorbed. The mixture is filtered and the solvent is removed in vacuo to give 4-[(2,2-dichloro-1-methylcyclopropyl)methyl]-o-phenylene diamine as a dark oil which is used immediately in the following reaction.

To a mixture of 6 g of 2-methyl-2-thiopseudourea sulfate in 6 ml of $H_2O$, there is added 5.7 ml of methylchloroformate at 0° C and the mixture is stirred for 15 minutes. Then there is added 14 ml of 25% NaOH dropwise and the mixture is stirred for 15 minutes. Then there is added 6 ml of acetic acid dropwise and the mixture is stirred for 15 minutes. Then the entire amount of the phenylenediamine from the preceding reaction in 20 ml of MeOH is added and the mixture is refluxed for 3 hours. The alcohol is removed in vacuo and $H_2O$ is added. The resulting solid is filtered off and crystallized from MeCN to yield 4.9 g of the title compound, m.p. 175–178°.

Anal calcd for $C_{14}H_{15}Cl_2N_3O_2S$: C, 46.68; H, 4.20; N, 11.66. Found: C, 46.94; H, 4.38; N, 11.83.

B.

[5-[[(2,2-Dichloro-1-methylcyclopropyl)methyl]-sulfinyl]-1H-benzimidazol-2-yl]carbamic acid, methyl ester To a solution of 7.2 g (0.2 mole) of [5-[[(2,2-dichloro-1-methylcyclopropyl)methyl]thio]-1H-benzimidazol-2-yl]carbamic acid, methyl ester in 120 ml of $CHCl_3$ and 120 ml of acetic acid at −15° C there is added 4.2 g (0.02 mole) of 85% m-chloroperoxybenzoic acid and 40 ml of CHCl₃ and with stirring is allowed to warm to room temperature. The mixture is stirred for an additional 2 hours. The CHCl₃ is removed in vacuo and the remaining solution is neutralized with aqueous NaHCO₃. The resulting solid is filtered off, dried, and crystallized from acetonitrile to yield 3.4 g of the title compound, m.p. 231–233° C.

Anal Calcd for $C_{14}H_{15}N_3O_3Cl_2S$: C, 44.69; H, 4.02; N, 11.17. Found: C, 44.83; H, 3.82; N, 11.34.

EXAMPLE 3

[5-[(2,2-Dichloro-1-methylcyclopropylmethyl)sulfinyl]-1H-benzimidazol-2-yl]-carbamic acid, benzyl ester Following the procedure of Example 1 and substituting benzyl chloroformate for methyl chloroformate and substituting 1-bromomethyl-1-methyl-2,2-dichlorocyclopropane for 1-bromomethyl-2,2-dichlorocyclopropane, the title compound is obtained.

EXAMPLE 4

[5-[(2,3-Dimethylcyclopentyl-1-methylethyl)sulfinyl]-1H-benzimidazol-2-yl]carbamic acid, methyl ester Following the procedure of Example 1 and substituting 1-(2-chloro-i-propyl)-2,3-dimethyl-3-cyclopentane for 1-bromomethyl-2,2-dichlorocyclopropane, the title compound is obtained.

EXAMPLES 5 to 16

Following the procedure of Example 1 except substituting for cyclohexylmethyl bromide the compound shown in column I of Table I below and substituting for methyl chloroformate the compound shown in column II, the product shown in column III is obtained.

TABLE I

| | Column I | | Column II | Column III | |
|---|---|---|---|---|---|
| | $R^4-(CH_2)_m-\underset{R^3}{\overset{R^2}{C}}-(CH_2)_n-X$ | | $HCOOR^1$ | $R^4-(CH_2)_m-\underset{R^3}{\overset{R^2}{C}}-(CH_2)_n-S\overset{O}{\underset{\uparrow}{-}}\underset{\underset{H}{N}}{\overset{N}{\diagdown}}NHCO_2R'$ | |
| Ex. No. | $R^4$ | $-(CH_2)_m-\underset{R^3}{\overset{R^2}{C}}-(CH_2)_n-$ | X  $R^1$ | $R^4-(CH_2)_m-\underset{R^3}{\overset{R^2}{C}}-(CH_2)_n$ | $R^1$ |
| 5. | (chlorinated cyclobutane with Cl, Cl) | $-\underset{\|}{CH}-CH_2CH_3$ | Cl  n-C₃H₇ | as in Column I | as in Column II |
| 6. | (cyclohexyl with Br) | $-\underset{\|}{CH}-C_2H_5$ | Br  C₂H₄Cl | | |
| 7. | (cycloheptyl with Br, Br) | $-\underset{CH_3}{\overset{CH_3}{C}}-$ | Cl  CH₃ | | |
| 8. | (cyclooctane with Cl) | $-(CH_2)_2-$ | Br  C₂H₅ | | |
| 9. | (C₁₂ ring with CH₃) | $-CH_2-$ | Br  C₂H₅ | | |
| 10. | (cyclopentenyl) | $-\underset{\|}{CH}CH_2-C_2H_5$ | Cl  CH₂—C₆H₅ | | |
| 11. | (cyclopentenyl) | $-CH_2-$ | Br  CH₃ | | |
| 12. | (cyclohexenyl) | $-(CH_2)_2$ | Cl  C₂H₅ | | |
| 13. | (cycloheptyl with C₂H₅) | $-(CH_2)_2-$ | Cl  n-C₄H₉ | | |
| 14. | (C₁₀ ring) | $-CH_2-$ | Br  C₂H₄C₆H₅ | | |

TABLE I-continued

| | Column I | | Column II | Column III |
|---|---|---|---|---|
| | $R^4-(CH_2)_m-\underset{R^3}{\overset{R^2}{C}}-(CH_2)_n-X$ | | $HCOOR^1$ | $R^4-(CH_2)_m-\underset{R^3}{\overset{R^2}{C}}-(CH_2)_n-\overset{\overset{O}{\uparrow}}{S}-\underset{\underset{H}{N}}{\underset{|}{\diagdown}}\underset{NHCO_2R'}{\overset{N}{\diagup}}$ |
| Ex. No. | $R^4$ | $-(CH_2)_m-\underset{R^3}{\overset{R^2}{C}}-(CH_2)_n-$ | X  $R^1$ | $R^4-(CH_2)_m-\underset{R^3}{\overset{R^2}{C}}-(CH_2)_n$  $R^1$ |
| 15. | 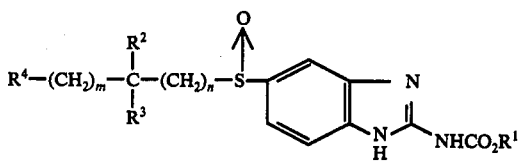 | $-\underset{|}{\overset{CH_3}{CH}}-$ | Cl  $CH_3$ | |
| 16. | (cyclododecyl with $C_2H_5$) | $-CH_2-$ | Br  $CH_3$ | |

EXAMPLE 17

An injectable suspension is prepared by suspending 100 mg of [5-[(2,2-dichlorocyclopropyl)methylsulfinyl]-1H-benzimidazol-2-yl]carbamic acid, methyl ester in 8 cc water for injection USP.

What is claimed is:

1. A compound of the structure $$R^4-(CH_2)_m-\underset{R^3}{\overset{R^2}{\underset{|}{C}}}-(CH_2)_n-\overset{\overset{O}{\uparrow}}{S}-\underset{\underset{H}{N}}{\underset{|}{\diagdown}}\underset{NHCO_2R^1}{\overset{N}{\diagup}}$$

wherein $R^1$ is lower alkyl containing 1 to 7 carbons or phenyl-lower alkyl containing 1 to 7 carbons in the alkyl group, $R^2$ and $R^3$ are the same or different and are selected from the group consisting of hydrogen or lower alkyl containing 1 to 7 carbons, and $R^4$ is selected from the group consisting of halocycloalkyl containing 3 to 12 carbons or cycloalkenyl containing 3 to 10 carbons optionally substituted with alkyl containing 1 to 7 carbons or halo, $m$ is 0 to 3, $n$ is 0 to 3 and $m + n \leq 5$.

2. The compound as defined in claim 1 wherein $R^1$ is lower alkyl or benzyl.

3. The compound as defined in claim 1 wherein $R^1$ is methyl ethyl, propyl or benzyl, $m$ is 0, $n$ is 0 or 1, $R^2$ is hydrogen or methyl and $R^3$ is hydrogen and $R^4$ is 2,2-dichlorocyclopropyl or cyclohexen-3-yl.

4. The compound as defined in claim 1 wherein $m$ is 0 and $n$ is 0, and $R^2$ and $R^3$ are hydrogen.

5. The compound as defined in claim 1 wherein $R^4$ is halocycloalkyl.

6. The compound as defined in claim 1 wherein $R^4$ is cycloalkenyl.

7. The compound as defined in claim 5 having the name [5-[(2,2-dichlorocyclopropylmethyl)sulfinyl]-1H-benzimidazol-2-yl]carbamic acid, methyl ester.

8. A pharmaceutical composition for use as an anthelmintic agent comprising an effective amount of a compound as defined in claim 1 and a pharmaceutically acceptable carrier therefor.

9. A method for treating helminthiasis which comprises administering to a mammalian host an effective amount of a pharmaceutical composition comprising an effective amount of a compound as defined in claim 1 and a pharmaceutically acceptable carrier therefor.

10. The method as defined in claim 9 wherein said compound is administered parenterally.

11. The method as defined in claim 10 wherein said compound is administered subcutaneously.

12. A compound having the name [5-[[(2,2-dichloro-1-methylcyclopropyl)methyl]sulfinyl]-1H-benzimidazol-2-yl]carbamic acid, methyl ester.

13. A compound having the name [5-[(2,2-dichloro-1-methylcyclopropylmethyl)sulfinyl]-1H-benzimidazol-2-yl]carbamic acid, benzyl ester.

* * * * *

UNITED STATES PATENT AND TRADEMARK OFFICE
CERTIFICATE OF CORRECTION

PATENT NO. : 4,093,732
DATED : June 6, 1978
INVENTOR(S) : Rudiger D. Haugwitz et al.

It is certified that error appears in the above-identified patent and that said Letters Patent are hereby corrected as shown below:

In the Abstract, next to the last line, "<" should read --$\leq$--.
Examples 15 and 16, Column III, under the column entitled
"$R^4-(CH_2)_m-\underset{\underset{R^3}{|}}{\overset{\overset{R^2}{|}}{C}}-(CH_2)_n$" insert --as in Column I--.

Examples 15 and 16, Column III, under the column entitled "$R^1$" insert --as in Column II--.

Signed and Sealed this

Fourteenth Day of November 1978

[SEAL]

Attest:

RUTH C. MASON
Attesting Officer

DONALD W. BANNER
Commissioner of Patents and Trademarks